United States Patent
Akabori et al.

(10) Patent No.: US 10,441,815 B2
(45) Date of Patent: Oct. 15, 2019

(54) NEUTRON CAPTURE THERAPY SYSTEM AND GAMMA RAY DETECTOR FOR NEUTRON CAPTURE THERAPY

(71) Applicants: SUMITOMO HEAVY INDUSTRIES, LTD., Tokyo (JP); Kyoto University, Kyoto (JP)

(72) Inventors: Kiyotaka Akabori, Kanagawa (JP); Hiroki Tanaka, Kyoto (JP)

(73) Assignees: SUMITOMO HEAVY INDUSTRIES, LTD., Tokyo (JP); KYOTO UNIVERSITY, Kyoto (JP)

( * ) Notice: Subject to any disclaimer, the term of this patent is extended or adjusted under 35 U.S.C. 154(b) by 94 days.

(21) Appl. No.: 15/925,234

(22) Filed: Mar. 19, 2018

(65) Prior Publication Data
US 2018/0280726 A1 Oct. 4, 2018

(30) Foreign Application Priority Data

Mar. 29, 2017 (JP) .................. 2017-066025

(51) Int. Cl.
*A61N 5/10* (2006.01)
*G01T 1/00* (2006.01)
(Continued)

(52) U.S. Cl.
CPC ............ *A61N 5/1048* (2013.01); *G01T 1/003* (2013.01); *G01T 1/161* (2013.01); *G01T 1/20* (2013.01);
(Continued)

(58) Field of Classification Search
CPC .......... A61N 2005/1094; A61N 5/1048; A61N 2005/109
See application file for complete search history.

(56) References Cited

U.S. PATENT DOCUMENTS

| | | | |
|---|---|---|---|
| 6,011,266 A | 1/2000 | Bell | |
| 7,208,743 B2 | 4/2007 | Luszik-Bhadra et al. | |
| 2015/0105604 A1* | 4/2015 | Liu | ..................... A61N 5/1077 600/1 |

FOREIGN PATENT DOCUMENTS

| | | |
|---|---|---|
| JP | 2001-242101 A | 9/2001 |
| JP | 2004-037106 A | 2/2004 |

(Continued)

OTHER PUBLICATIONS

Anonymous: "Neutron shielding," Retrieved from the internet: www- eng.lbl.gov/~dw/projects/DW4132_BORG_Fission_Source/bor%20PE.pdf, XP055493174, model JC215 shown on p. 2, pp. 1-7.

(Continued)

*Primary Examiner* — Kenneth J Malkowski
(74) *Attorney, Agent, or Firm* — Michael Best & Friedrich LLP (57) ABSTRACT

A neutron capture therapy system includes a neutron ray generating unit, an irradiated body placing unit on which a patient (irradiated body) is placed, and a gamma ray detecting unit that detects gamma rays emitted from the patient (irradiated body). The gamma ray detecting unit includes an emission part that emits light or electrons as the gamma rays are incident thereon, an amplification part that amplifies and outputs the light or the electrons emitted from the emission part, a first neutron ray shielding part formed of a substance containing 6-lithium, and a second neutron ray shielding part formed of a light element. The first neutron ray shielding part is provided so as to cover at least a surface opposite to an adjacent surface adjacent to the amplification part, among surfaces of the emission part.

5 Claims, 4 Drawing Sheets

(51) Int. Cl.
  *G01T 1/161*  (2006.01)
  *G01T 1/29*  (2006.01)
  *G01T 1/20*  (2006.01)
  *G01T 1/24*  (2006.01)
  *G01T 3/06*  (2006.01)
  *G01T 3/08*  (2006.01)

(52) U.S. Cl.
  CPC .................. *G01T 1/24* (2013.01); *G01T 1/29* (2013.01); *G01T 3/06* (2013.01); *G01T 3/08* (2013.01); *A61N 2005/109* (2013.01); *A61N 2005/1094* (2013.01); *A61N 2005/1098* (2013.01)

(56) References Cited

FOREIGN PATENT DOCUMENTS

| | | | | |
|---|---|---|---|---|
| JP | 2004-534257 A | 11/2004 | | |
| JP | 2016-159107 A | 9/2016 | | |
| JP | 2016-214760 A | 12/2016 | | |
| WO | WO-03/007018 A2 | 1/2003 | | |
| WO | WO-2006089097 A2 * | 8/2006 | ............... | G01T 3/00 |
| WO | WO-2014156245 A1 * | 10/2014 | ........... | A61N 5/1048 |

OTHER PUBLICATIONS

Extended Search Report issued in European Patent Application No. 18161365.4, dated Jul. 30, 2018.

* cited by examiner

NEUTRON CAPTURE THERAPY SYSTEM AND GAMMA RAY DETECTOR FOR NEUTRON CAPTURE THERAPY

RELATED APPLICATIONS

Priority is claimed to Japanese Patent Application No. 2017-066025, filed Mar. 29, 2017, the entire content of which is incorporated herein by reference.

BACKGROUND

Technical Field

Certain embodiments of the present invention relate to a neutron capture therapy system and a gamma ray detector for neutron capture therapy.

Description of Related Art

As one of radiation therapy methods in cancer treatment or the like, there is a boron neutron capture therapy (BNCT) in which cancer treatment is performed by radiation of neutron rays. In the boron neutron capture therapy, tumor cells are destroyed by radiating neutron rays to an affected part of a patient to whom medicine including boron is administered and causing a reaction between boron and neutrons in the tumor cell.

In such a boron neutron capture therapy, it is desired to measure the concentration of boron in a patient's body in real time. In the related art, a neutron capture therapy apparatus that includes a gamma ray detector that detects gamma rays generated by a reaction between neutron rays and boron and is capable of calculating the concentration of boron in a patient's body from information on the gamma rays detected by the gamma ray detecting unit is disclosed.

Since the treatment environment of the neutron capture therapy becomes a high-intensity neutron field, the gamma ray detector is likely to deteriorate. For this reason, there is a concern that the detection accuracy of the gamma rays may decline. Hence, even in the high-intensity neutron field, it is requested to detect the gamma rays with high accuracy.

SUMMARY

According to one aspect of the invention, there is provided a neutron capture therapy system including: a neutron ray generating unit that generates neutron rays; an irradiated body placing unit on which an irradiated body irradiated with the neutron rays is placed; and a gamma ray detecting unit that detects gamma rays emitted from the irradiated body by being irradiated with the neutron rays. The gamma ray detecting unit includes an emission part that emits light or electrons as the gamma rays are incident thereon, an amplification part that is provided adjacent to the emission part and amplifies and outputs the light or the electrons emitted from the emission part, a first neutron ray shielding part formed of a substance containing 6-lithium, and a second neutron ray shielding part provided outside the first neutron ray shielding part and formed of a light element. The first neutron ray shielding part is provided so as to cover at least a surface opposite to an adjacent surface adjacent to the amplification part, among surfaces of the emission part.

According to another aspect of the invention, there is provided a gamma ray detector for neutron capture therapy including: an emission part that emits light or electrons as gamma rays are incident thereon; an amplification part that is provided adjacent to the emission part and amplifies and outputs the light or the electrons emitted from the emission part; a first neutron ray shielding part formed of a substance containing 6-lithium; and a second neutron ray shielding part provided outside the first neutron ray shielding part and formed of a light element. The first neutron ray shielding part is provided so as to cover at least a surface opposite to an adjacent surface adjacent to the amplification part, among surfaces of the emission part.

DETAILED DESCRIPTION

The invention has been made in order to solve such problems and an object thereof is to provide a neutron capture therapy system and a gamma ray detector for neutron capture therapy capable of detecting gamma rays with high accuracy even in a high-intensity neutron field.

In this neutron capture therapy system, the gamma ray detecting unit has the first neutron ray shielding part formed of the substance containing 6-lithium, and the second neutron ray shielding part provided outside the first neutron ray shielding part and formed of the light element. Since the neutron rays that are incident on the emission part of the gamma ray detecting unit are shielded by the first neutron ray shielding part and the second neutron ray shielding part, deterioration of the emission part can be suppressed. Additionally, since 6-lithium has a higher function of shielding the neutron rays than the light element, the neutron rays that are incident on the emission part can be reliably shielded. Hence, even in a high-intensity neutron field, it is possible to suppress deterioration of the emission part and to detect the gamma rays with high accuracy.

In the neutron capture therapy system according to the aspect, the gamma ray detecting unit may further have a gamma ray shielding part provided between the first neutron ray shielding part and the second neutron ray shielding part. According to this configuration, the incidence of the gamma rays into the emission part from the surfaces other than the surface opposite to the adjacent surface of the emission part adjacent to the amplification part can be suppressed.

In the neutron capture therapy system according to the aspect, the first neutron ray shielding part may be provided so as to cover surfaces other than the adjacent surface among the surfaces of the emission part. According to this configuration, it is possible to more reliably shield the neutron rays that are incident on the emission part.

In the neutron capture therapy system according to the aspect, a thickness of the first neutron ray shielding part that covers the surface opposite to the adjacent surface may be greater than thicknesses of the first neutron ray shielding part that covers the other surfaces of the emission part. The dose of neutrons that are incident on the other surfaces is smaller than the dose of neutrons that are incident on the surface opposite to the adjacent surface. Hence, as the thickness of the first neutron ray shielding part that covers the surface of the emission part having a smaller incidence amount of the neutron rays is made relatively small, the amount of expensive 6-lithium used can be reduced.

In this gamma ray detector for neutron capture therapy, the gamma ray detector includes the first neutron ray shielding part formed of the substance containing 6-lithium, and the second neutron ray shielding part provided outside the first neutron ray shielding part and formed of the light element. Since the neutron rays that are incident on the emission part of the gamma ray detecting unit are shielded by the first neutron ray shielding part and the second neutron ray shielding part, deterioration of the emission part can be suppressed. Additionally, since 6-lithium has a higher function of shielding the neutron rays than the light element, the neutron rays that are incident on the emission part can be reliably shielded. Hence, even in a high-intensity neutron field, it is possible to suppress deterioration of the emission part and to detect the gamma rays with high accuracy.

According to the invention, there is provided the neutron capture therapy system and the gamma ray detector for neutron capture therapy capable of detecting the gamma rays with high accuracy even in a high-intensity neutron field.

Hereinafter, various embodiments of the invention will be described in detail with reference to the drawings. In addition, the same or equivalent parts in the respective drawings will be designated by the same reference signs, and duplicate description thereof will be omitted.

Figure 1:
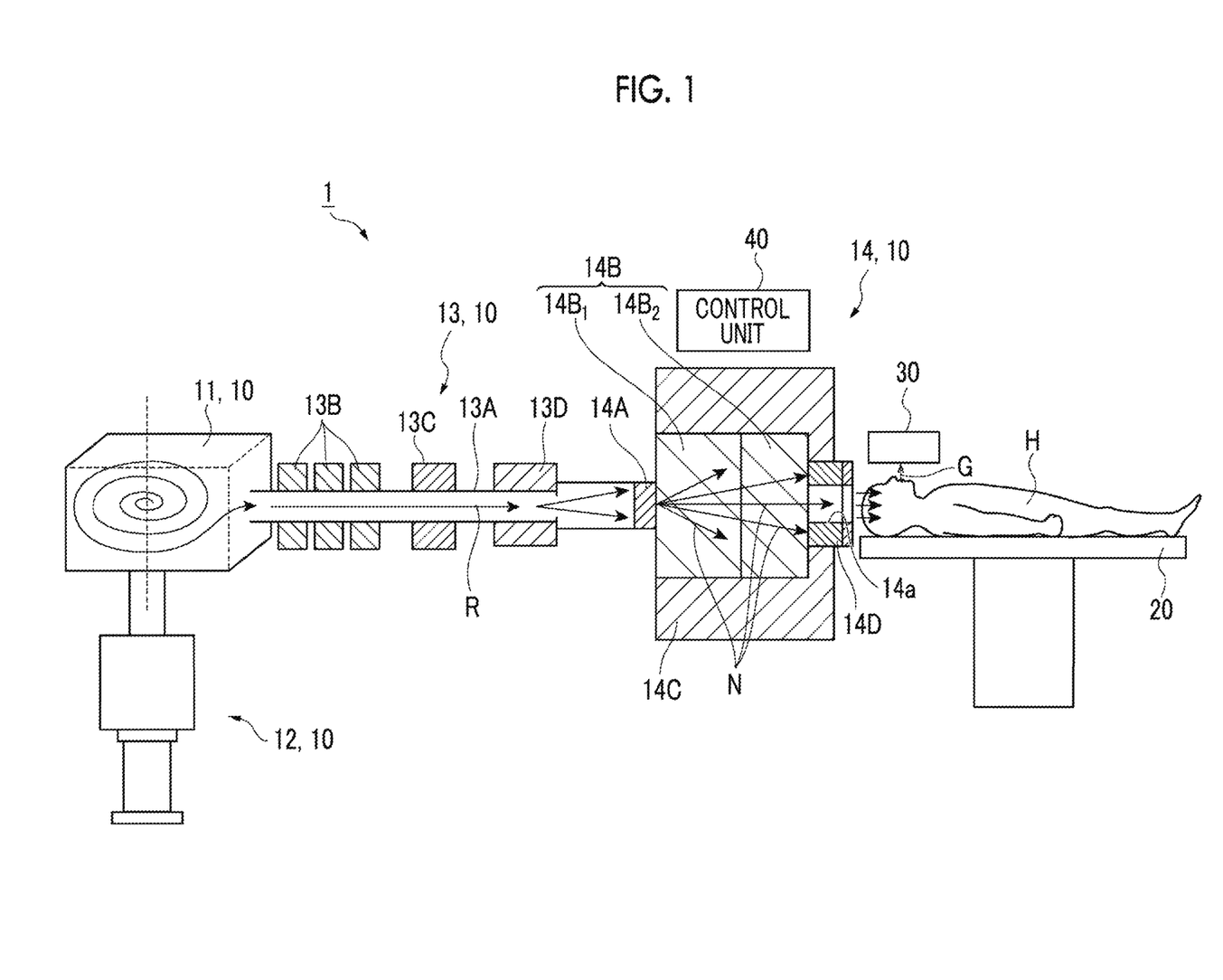
FIG. 1 is a view schematically illustrating a neutron capture therapy system according to an embodiment of the invention.

FIG. 1 is a view schematically illustrating a neutron capture therapy system according to an embodiment of the invention. A neutron capture therapy system 1 illustrated in FIG. 1 is an apparatus that performs cancer treatment using boron neutron capture therapy (BNCT). In the neutron capture therapy system 1, for example, a tumor of a patient (irradiated body) H to which medicine including boron (10B) has been administered is irradiated with neutron rays N.

The neutron capture therapy system 1 includes a neutron ray generating unit 10 that generates neutron rays, an irradiated body placing unit 20 on which the patient H irradiated with neutron rays is placed, and a gamma ray detecting unit 30 that detects gamma rays G emitted from the patient H.

The neutron ray generating unit 10 has an accelerator 11, a negative ion source 12, a beam transporting part 13, and a neutron ray radiating part 14. The accelerator 11 accelerates negative ions (also referred to as anions) generated in the negative ion source 12 to generate a charged particle beam P. The accelerator 11 is, for example, a cyclotron. The accelerator 11 has, for example, the capability of generating a charged particle beam P having a beam radius of 40 mm and 60 kW (=30 MeV×2 mA). In addition, the accelerator 11 is not limited to the cyclotron, and may be, for example, a synchrotron, a synchro-cyclotron, a linac, or the like. Additionally, the neutron ray generating unit may be a nuclear reactor.

The charged particle beam P emitted from the accelerator 11 is introduced into the beam transporting part 13. The beam transporting part 13 has abeam duct 13A, a four-pole electromagnet 13B, an electric current monitor 13C, and a scanning electromagnet 13D. The accelerator 11 is connected to one end side of the beam duct 13A, and the neutron ray radiating part 14 is connected to the other end side of the beam duct 13A. The charged particle beam P passes through the beam duct 13A, and travels toward the neutron ray radiating part 14.

A plurality of the four-pole electromagnets 13B is provided along the beam duct 13A, and adjusts the beam axis of the charged particle beam P, using the electromagnets. The electric current monitor 13C detects the current value (that is, electric charges, an irradiation dose rate) of the charged particle beam P in real time. As the electric current monitor 13C, for example, a non-destructive DC current transformer (DCCT) capable of performing current measurement without influencing the charged particle beam P is used. That is, the electric current monitor 13C can detect the current value of the charged particle beam P without coming into contact with the charged particle beam P (in a contactless manner). The electric current monitor 13C outputs a detection result to a control unit 40 to be described below. In addition, the "dose rate" means dose per unit time.

Specifically, in order to accurately detect the current value of the charged particle beam P to be radiated to a target 14A of the neutron ray radiating part 14, the electric current monitor 13C is provided immediately in front of the scanning electromagnet 13D downstream of the four-pole electromagnets 13B (downstream of the charged particle beam P) so as to eliminate the influence of the four-pole electromagnets 13B. That is, since the scanning electromagnet 13D scans the target 14A such that the charged particle beam P is not always radiated to the same position, a large-sized electric current monitor 13C is required for disposing the electric current monitor 13C downstream of the scanning electromagnet 13D. In contrast, the electric current monitor 13C can be downsized by providing the electric current monitor 13C upstream of the scanning electromagnet 13D.

The scanning electromagnet 13D performs scanning with the charged particle beam P, and controls the radiation of the charged particle beam P to the target 14A. The scanning electromagnet 13D controls the position of radiation of the charged particle beam P to the target 14A.

By irradiating the target 14A with the charged particle beam P, the neutron ray radiating part 14 generates the neutron rays N and emits the neutron rays N toward the patient H. The neutron ray radiating part 14 includes the target 14A, a moderator 14B, a shielding body 14C, and a collimator 14D.

The target 14A generates the neutron rays N by being irradiated with the charged particle beam P. The target 14A herein is formed of, for example, beryllium (Be), lithium (Li), tantalum (Ta), tungsten (W), or the like and assumes a disk shape with a diameter of, for example, 160 mm. In addition, the target 14A is not limited to having the disk shape and may have other solid shapes. A liquid target (liquid metal) may be used.

The moderator 14B decelerates the neutron rays N generated in the target 14A to lower the energy of the neutron rays N. The moderator 14B has a laminated structure including a first moderator 14B1 that mainly decelerates fast neutron rays included in the neutron rays N, and a second moderator 14B2 that mainly decelerates epithermal neutron rays included in the neutron rays N.

The shielding body 14C shields the generated neutron rays N, secondary radiant rays, such as the gamma rays G generated in the target 14A with the generation of the neutron rays N, secondary radiant rays, such as the gamma rays G generated in the moderator 14B when the neutron rays N are decelerated by the moderator 14B, and suppresses emission of these radiant rays to the patient H side. The shielding body 14C is provided so as to surround the moderator 14B.

The collimator 14D shapes the radiation field of the neutron rays N, and has an opening 14a through which the neutron rays N pass. The collimator 14D is, for example, a block-shaped member having the opening 14a at the center thereof.

The irradiated body placing unit 20 is configured to be capable of adjusting the height, and the like of the patient H such that a tumor of the patient H is irradiated with the neutron rays N emitted from the opening 14a of the collimator 14D. The neutron capture therapy system 1 includes, for example, an irradiation chamber for irradiating the patient H with the neutron rays N, and the irradiated body placing unit 20 may be disposed in the irradiation chamber. The irradiation chamber may be surrounded by a shielding wall that suppresses penetration of radiant rays from the outside of the chamber to the inside of the chamber and emission of radiant rays from the inside of the chamber to the outside of the chamber.

The gamma ray detecting unit 30 is provided for measuring the concentration of boron in the body of the patient H in real time during the radiation of the neutron rays N. The gamma ray detecting unit 30 detects the gamma rays G generated from a reaction between neutrons and boron to measure the concentration of boron. The gamma ray detecting unit 30 is disposed, for example, in the vicinity of the tumor of the patient H in order to detect the gamma rays G emitted from the patient H. The detailed configuration of the gamma ray detecting unit 30 will be described below.

Additionally, the neutron capture therapy system 1 includes the control unit 40. The control unit 40 is constituted of a central processing unit (CPU), a read-only memory (ROM), a random access memory (RAM), and the like, and is an electronic unit that comprehensively controls the neutron capture therapy system 1.

Figure 2:
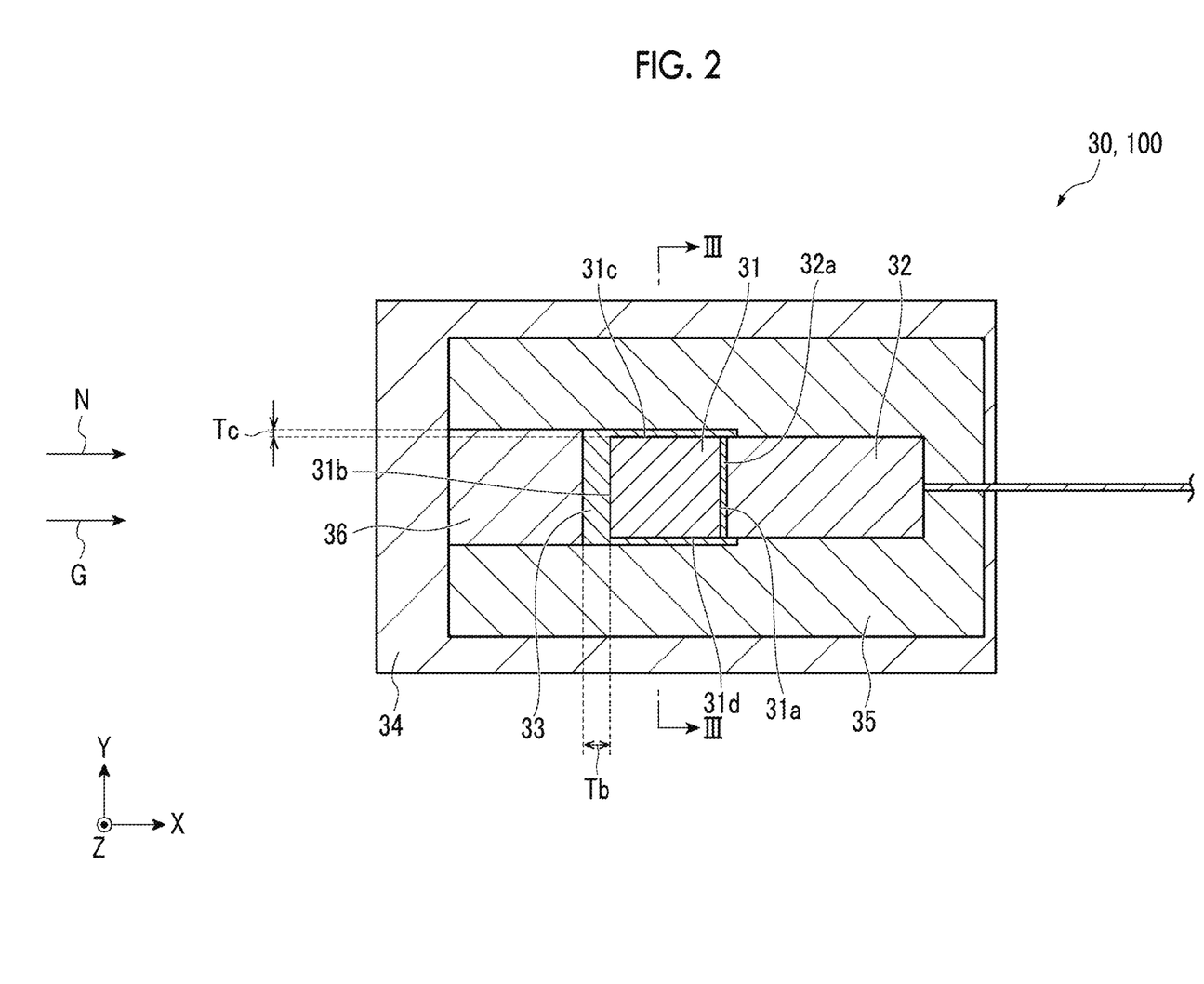
FIG. 2 is a sectional view schematically illustrating a gamma ray detecting unit.
Figure 3:
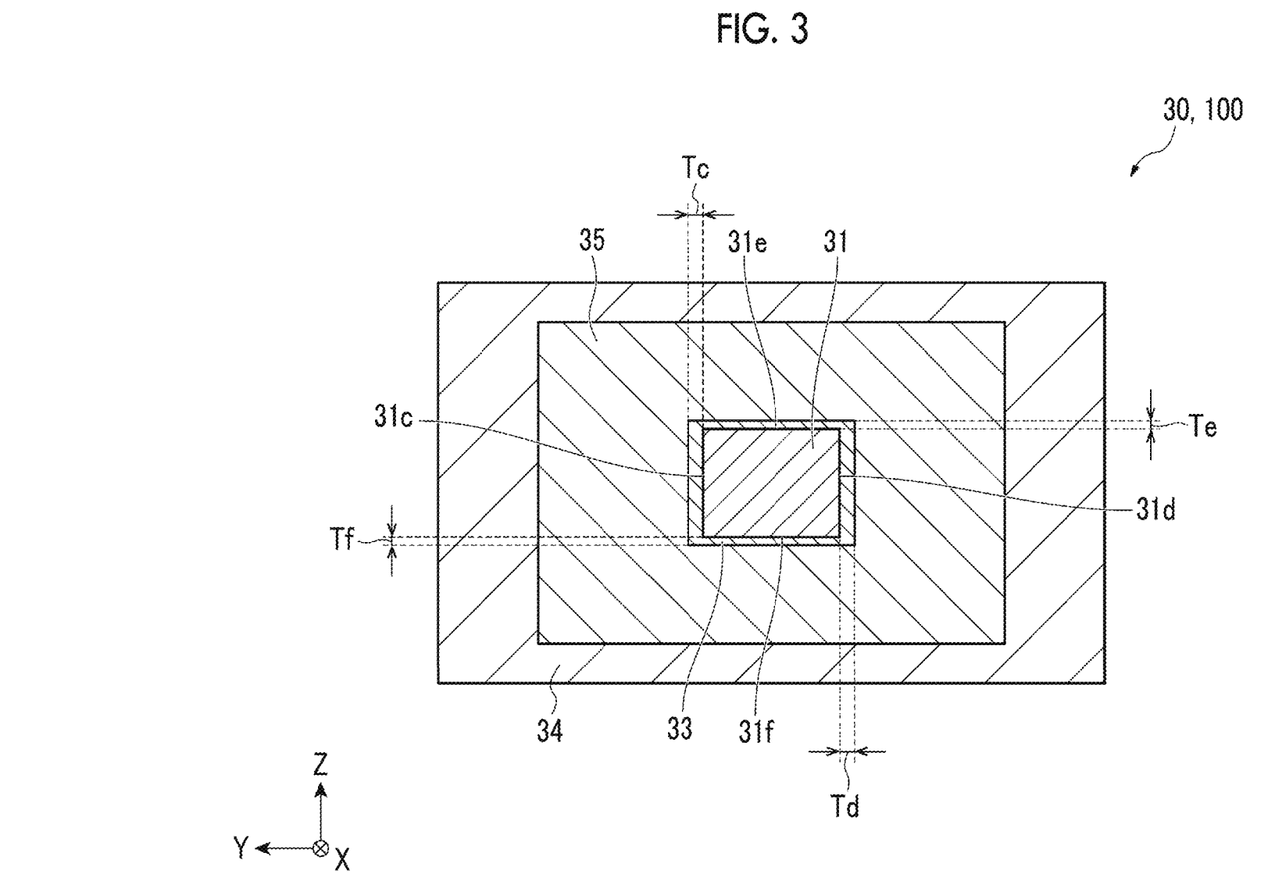
FIG. 3 is a view illustrating a section taken along line III-III of FIG. 2.

Next, the gamma ray detecting unit 30 will be described in detail with reference to FIGS. 2 and 3. FIG. 2 is a sectional view schematically illustrating the gamma ray detecting unit. FIG. 3 is a view illustrating a section taken along line III-III of FIG. 2.

As illustrated in FIGS. 2 and 3, the gamma ray detecting unit 30 has an emission part 31, an amplification part 32, a first neutron ray shielding part 33, and a second neutron ray shielding part 34. Additionally, the gamma ray detecting unit 30 has a gamma ray shielding part 35 and a gamma ray detecting collimator 36 that are provided between the first neutron ray shielding part 33 and the second neutron ray shielding part 34. Hereinafter, a direction in which the gamma rays G from the patient H are incident without being deflected is defined as an X-axis direction, an upward-downward direction is defined as a Z-axis direction, and a direction orthogonal to the X-axis direction and the Z-axis direction is defined as a Y-axis direction. Particularly, the traveling direction of the gamma rays G is defined as an X-axis normal direction.

The gamma ray detecting collimator 36, the emission part 31, and the amplification part 32 are disposed in order in the X-axis direction. The first neutron ray shielding part 33 is disposed so as to cover the emission part 31. The gamma ray shielding part 35 is provided so as to cover the gamma ray detecting collimator 36, the emission part 31, the amplification part 32, and the first neutron ray shielding part 33. The second neutron ray shielding part 34 is provided so as to cover the gamma ray detecting collimator 36, the emission part 31, the amplification part 32, the first neutron ray shielding part 33, and the gamma ray shielding part 35.

The gamma ray detecting collimator 36 has a through-hole passing therethrough in the X-axis direction. The gamma ray detecting collimator 36 is formed of, for example, a material, such as lead, having a function of shielding the gamma rays G. The gamma rays G emitted from the patient H pass through the through-hole formed in the gamma ray detecting collimator 36, and are incident on the emission part 31. The gamma ray detecting collimator 36 is provided on an incidence surface 31b side of the emission part 31 to be described below.

The emission part 31 emits light or electrons due to the incidence of the gamma rays G from the patient H. The emission part 31 assumes, for example, a rectangular parallelepiped shape, and has an adjacent surface 31a (one surface on an X-axis positive side) adjacent to the amplification part 32, the incidence surface 31b (one surface on an X-axis negative side) that is located on a side opposite to the adjacent surface 31a and that the gamma rays G from the patient H are incident thereon, and four side surfaces 31c, 31d, 31e, and 31f that connect the adjacent surface 31a and the incidence surface 31b together. In the present embodiment, the emission part 31 is, for example, a scintillator. The scintillator 13 is a fluorescent body that converts incident radiant rays (the neutron rays N, the gamma rays G, and the like) into light. In the scintillator, internal crystals are brought into an excited state in accordance with the dose of the incident radiant rays, and generates scintillation light. As the scintillator, for example, LaBr3, LaCl3, CeBr, GaGG, SrI2, LuAG, or the like can be used. In addition, the emission part 31 may not be the scintillator, and may be a semiconductor element that emits electrons as radiant rays are incident thereon.

The amplification part 32 amplifies and outputs the light or the electrons emitted from the emission part 31. The amplification part 32 is provided so as to be in contact with the emission part 31. More specifically, the amplification part 32 is provided on the adjacent surface 31a side (X-axis positive side) of the emission part 31. In the present embodiment, one surface of the amplification part 32 in contact with the emission part 31 is provided with an incidence window 32a, and the amplification part 32 amplifies the light emitted from the emission part 31. As the amplification part 32, for example, a photodetector, such as a photomultiplier tube or a photoelectric tube, or a semiconductor photodetector, such as APD or SiPM, can be adopted. A signal amplified by the amplification part 32 is output to, for example, the control unit 40.

The first neutron ray shielding part 33 is for suppressing incidence of the neutron rays N to the emission part 31. The first neutron ray shielding part 33 is provided so as to cover at least the surface of the emission part 31 opposite to the adjacent surface 31a adjacent to the amplification part 32, that is, the incidence surface 31b. In the present embodiment, the first neutron ray shielding part 33 is provided so as to cover surfaces (the incidence surface 31b and the side surfaces 31c, 31d, 31e, and 31f) other than the adjacent surface 31a adjacent to the amplification part 32. Additionally, in order to suppress the incidence of the neutron rays N from the incidence window 32a of the amplification part 32, the first neutron ray shielding part 33 is provided so as to cover the incidence window 32a and a portion of the amplification part 32.

In the present embodiment, a thickness Tb of the first neutron ray shielding part 33 that covers the incidence surface 31b of the emission part 31 is greater than thicknesses Tc, Td, Te, and Tf of the first neutron ray shielding part 33 that covers the side surfaces 31c, 31d, 31e, and 31f (other surfaces of the emission part 31). Additionally, the thicknesses Tc, Td, Te, and Tf of the first neutron ray shielding part 33 can be appropriately set in accordance with an environment in which the gamma ray detecting unit 30 is disposed. For example, in a case where the gamma ray detecting unit 30 is disposed in an environment in which the incidence of the neutron rays N in the Y-axis direction is large, as illustrated in FIG. 3, the thicknesses Tc and Td of the first neutron ray shielding part 33 that covers the side surfaces 31c and 31d of the emission part 31 in the Y-axis direction can be set to be greater than the thicknesses Te and Tf of the first neutron ray shielding part 33 that covers the side surfaces 31e and 31f of the emission part 31 in the Z-axis direction.

The first neutron ray shielding part 33 is formed of, for example, a substance containing 6-lithium in which a function of shielding the neutron rays N is high and the emission of the gamma rays G caused by the incidence of the neutron rays N is little. Specifically, the first neutron ray shielding part 33 can be formed of a substance, such as 6-lithium fluoride, a 6Li glass scintillator, a 6LiCAF scintillator, a plastic scintillator coated with 6LiF, or 6 LiF/ZnS scintillator, having a function of shielding the neutron rays N. It is preferable that the content of 6-lithium is equal to or more than 11% to 24%. In a case where the first neutron ray shielding part 33 is formed of a substance containing 6-lithium fluoride, the thickness Tb of the first neutron ray shielding part 33 that covers the incidence surface 31b of the emission part 31 can be, for example, about 1 mm to about 2 mm.

Similar to the first neutron ray shielding part, the second neutron ray shielding part 34 is for suppressing incidence of the neutron rays N to the emission part 31. The second neutron ray shielding part 34 is provided outside the first neutron ray shielding part 33. The thickness of the second neutron ray shielding part 34 on the incidence surface 31b side (on the X-axis negative side of the gamma ray detecting unit 30) of the emission part 31 is provided to be greater than the thickness of the second neutron ray shielding part 34 in the other portions. Additionally, similar to the thickness of the first neutron ray shielding part 33, the thickness of the second neutron ray shielding part 34 can be appropriately set in accordance with the environment in which the gamma ray detecting unit 30 is disposed. For example, in a case where the gamma ray detecting unit 30 is disposed in an environment in which the incidence of the neutron rays N in the Y-axis direction is large, the thickness of the second neutron ray shielding part 34 on the side surface 31c side of the emission part 31 and the side surface 31d side (both end sides in the Y-axis direction) can be set to be greater than the thickness of the second neutron ray shielding part 34 on the side surface 31e side and the side surface 31f (both end sides in the Z-axis direction) side of the emission part 31. The second neutron ray shielding part 34 is formed of, for example, a light element including hydrogen. Here, the light element means an element having an atomic number of 20 or less.

The gamma ray shielding part 35 is for suppressing incidence of that gamma rays G into the emission part 31 from surfaces other than the incidence surface 31b. The gamma ray shielding part 35 is provided between the first neutron ray shielding part 33 and the second neutron ray shielding part 34. More specifically, the gamma ray shielding part 35 is provided on the adjacent surface 31a side (X-axis positive side) of the emission part 31, on the side surface 31c side and the side surface 31d side (both end sides in the Y-axis direction) of the emission part 31, and on the side surface 31e and the side surface 31f side (both end sides in the Z-axis direction) of the emission part 31. The gamma ray shielding part 35 is formed of, for example, a material, such as lead, containing a heavy element having a function of shielding the gamma rays G. Here, the heavy element means an element having a greater atomic number than 20.

The gamma ray detecting unit 30 can also be independently used as a gamma ray detector 100 for neutron capture therapy according to one form of the invention. Since the configuration of the gamma ray detector 100 for neutron capture therapy is the same as that of the gamma ray detecting unit 30, the description thereof will be omitted.

As described above, in the neutron capture therapy system 1, the gamma ray detecting unit 30 has the first neutron ray shielding part 33 formed of the substance containing 6-lithium, and the second neutron ray shielding part 34 provided outside the first neutron ray shielding part 33 and formed of the light element. Since the neutron rays N that are incident on the emission part 31 of the gamma ray detecting unit 30 are shielded by the first neutron ray shielding part 33 and the second neutron ray shielding part 34, deterioration of the emission part 31 can be suppressed. Additionally, since 6-lithium has a higher function of shielding the neutron rays N than the light element, the neutron rays N that are incident on the emission part 31 can be reliably shielded. Hence, even in a high-intensity neutron field, it is possible to suppress deterioration of the emission part and to detect the gamma rays G with high accuracy.

Additionally, the gamma ray detecting unit 30 further includes the gamma ray shielding part 35 provided between the first neutron ray shielding part 33 and the second neutron ray shielding part 34. Accordingly, the incidence of the gamma rays G into the emission part 31 from the surfaces other than the incidence surface 31b opposite to the adjacent surface 31a of the emission part 31 adjacent to the amplification part 32 can be suppressed. Additionally, as the gamma ray shielding part 35 is provided inside the second neutron ray shielding part 34, it is possible to shield the gamma rays G generated as the neutron rays N are incident on the second neutron ray shielding part 34.

Additionally, the first neutron ray shielding part 33 is provided so as to cover the surfaces other than the adjacent surface 31a among the surfaces of the emission part 31. Accordingly, it is possible to more reliably shield the neutron rays N that are incident on the emission part 31.

Additionally, the thickness of the first neutron ray shielding part 33 that covers the incidence surface 31b opposite to the adjacent surface 31a is greater than the thicknesses of the first neutron ray shielding part 33 that covers the other surfaces of the emission part 31. The doses of neutrons that are incident on the other surfaces are smaller than the dose of neutrons that are incident on the incidence surface 31b. Hence, as the thickness of the first neutron ray shielding part 33 that covers the surface of the emission part 31 having a smaller incidence amount of the neutron rays N is made relatively small, the amount of expensive 6-lithium used can be reduced.

Figure 4:
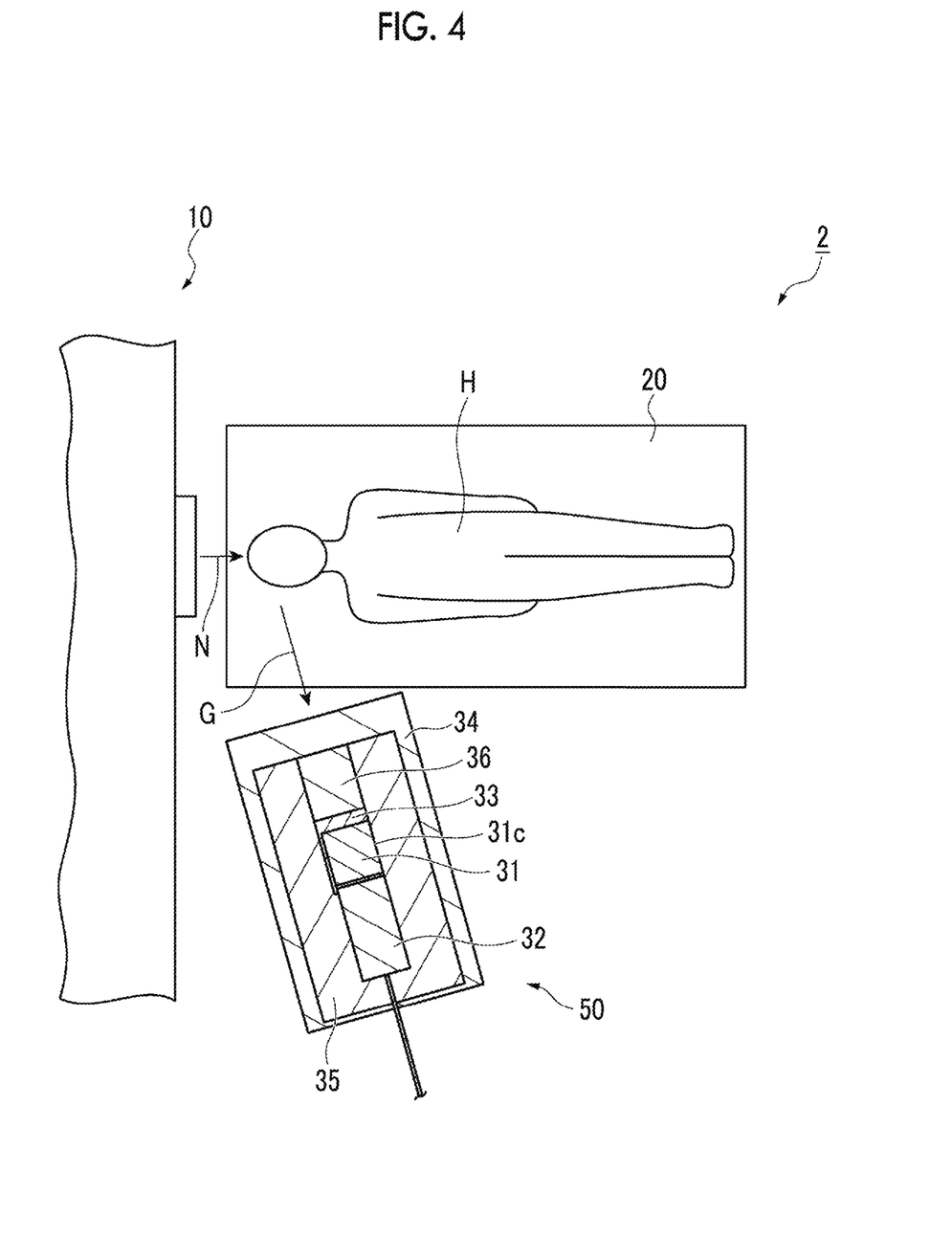
FIG. 4 is a view schematically illustrating a modification example of the neutron capture therapy system illustrated in FIG. 1.

Although the embodiment of the invention has been described above, the invention is not limited to the above embodiment, and various modified forms can be adopted. For example, in the above embodiment, the first neutron ray shielding part 33 is provided so as to cover the surfaces other than the adjacent surface 31a of the emission part 31. However, the shape of the first neutron ray shielding part 33 can be arbitrarily changed in accordance with the environment in which the gamma ray detecting unit 30 is disposed and the direction in which the gamma ray detecting unit 30 is disposed. FIG. 4 is a view schematically illustrating a modification example of the neutron capture therapy system illustrated in FIG. 1. As illustrated in FIG. 4, a neutron capture therapy system 2 includes a gamma ray detecting unit 50 instead of the gamma ray detecting unit 30. The gamma ray detecting unit 50 is disposed obliquely with respect to the neutron ray generating unit 10, and the side surface 31c of the emission part 31 located opposite to the neutron ray generating unit 10 is not covered with the first neutron ray shielding part 33. In such a neutron capture therapy system 2, the incidence amount of the neutron rays N from the side surface 31c side of the emission part 31 is smaller than the incidence amount of the neutron rays N from other directions. Thus, the side surface 31c of the emission part 31 does not need to be covered with the first neutron ray shielding part 33. Accordingly, the amount of 6-lithium used can be further reduced.

In addition, in the embodiment, the scintillator is used as the emission part 31. However, the emission part 31 may not be the scintillator, and may be a semiconductor element that emits electrons as radiant rays are incident thereon. In this case, the amplification part 32 may be an amplification circuit that amplifies electrons. Additionally, the emission part 31 and the amplification part 32 may be integrally provided.

In the above embodiment, the second neutron ray shielding part 34 is formed of the light element. However, the second neutron ray shielding part 34 may be formed of a substance in which lithium fluoride is made to contain polyethylene. Additionally, a resin material containing hydrogen, such as paraffin, may be used instead of polyethylene. Moreover, the second neutron ray shielding part 34 may be formed by laminating a resin material containing hydrogen, such as polyethylene, and lithium fluoride. In this case, since lithium fluoride has a higher function of shielding thermal neutrons than hydrogen and hydrogen has a higher function of shielding fast neutrons than lithium fluoride, a lithium fluoride layer is provided outside a layer of the resin material containing hydrogen. Accordingly, it is possible to effectively shield the neutron rays N.

Additionally, the gamma ray detector 100 for neutron capture therapy is not limited to being used for the neutron capture therapy and can be used for general detection of the gamma rays G.

It should be understood that the invention is not limited to the above-described embodiment, but may be modified into various forms on the basis of the spirit of the invention. Additionally, the modifications are included in the scope of the invention.

What is claimed is:

1. A neutron capture therapy system comprising:
   a neutron ray generating unit that generates neutron rays;
   an irradiated body placing unit on which an irradiated body irradiated with the neutron rays is placed; and
   a gamma ray detecting unit that detects gamma rays emitted from the irradiated body by being irradiated with the neutron rays,
   wherein the gamma ray detecting unit includes
   an emission part that emits light or electrons as the gamma rays are incident thereon,
   an amplification part that is provided adjacent to the emission part and amplifies and outputs the light or the electrons emitted from the emission part,
   a first neutron ray shielding part formed of a substance containing 6-lithium, and
   a second neutron ray shielding part provided outside the first neutron ray shielding part and formed of a light element, and
   wherein the first neutron ray shielding part is provided so as to cover at least a surface opposite to an adjacent surface adjacent to the amplification part, among surfaces of the emission part.

2. The neutron capture therapy system according to claim 1,
   wherein the gamma ray detecting unit further includes a gamma ray shielding part provided between the first neutron ray shielding part and the second neutron ray shielding part.

3. The neutron capture therapy system according to claim 1,
   wherein the first neutron ray shielding part is provided so as to cover surfaces other than the adjacent surface among the surfaces of the emission part.

4. The neutron capture therapy system according to claim 3,
   wherein a thickness of the first neutron ray shielding part that covers the surface opposite to the adjacent surface is greater than thicknesses of the first neutron ray shielding part that covers the other surfaces of the emission part.

5. A gamma ray detector for neutron capture therapy comprising:
   an emission part that emits light or electrons as gamma rays are incident thereon;
   an amplification part that is provided adjacent to the emission part and amplifies and outputs the light or the electrons emitted from the emission part;
   a first neutron ray shielding part formed of a substance containing 6-lithium; and
   a second neutron ray shielding part provided outside the first neutron ray shielding part and formed of a light element,
   wherein the first neutron ray shielding part is provided so as to cover at least a surface opposite to an adjacent surface adjacent to the amplification part, among surfaces of the emission part.

* * * * *